(12) United States Patent
Horner et al.

(10) Patent No.: US 8,968,308 B2
(45) Date of Patent: Mar. 3, 2015

(54) MULTI-CIRCUIT SEAL PLATES

(75) Inventors: Glenn A. Horner, Boulder, CO (US); Christina A. Oliver, Longmont, CO (US); Kim V. Brandt, Loveland, CO (US)

(73) Assignee: Covidien LP, Mansfield, MA (US)

( * ) Notice: Subject to any disclaimer, the term of this patent is extended or adjusted under 35 U.S.C. 154(b) by 692 days.

(21) Appl. No.: 13/277,373

(22) Filed: Oct. 20, 2011

(65) Prior Publication Data

US 2013/0103035 A1 Apr. 25, 2013

(51) Int. Cl.
*A61B 18/18* (2006.01)
*A61B 18/14* (2006.01)
*A61B 18/00* (2006.01)

(52) U.S. Cl.
CPC ......... *A61B 18/1442* (2013.01); *A61B 18/1445* (2013.01); *A61B 2018/00083* (2013.01); *A61B 2018/0016* (2013.01); *A61B 2018/00428* (2013.01); *A61B 2018/00607* (2013.01); *A61B 2018/0063* (2013.01); *A61B 2018/00642* (2013.01); *A61B 2018/00702* (2013.01); *A61B 2018/00791* (2013.01); *A61B 2018/00827* (2013.01); *A61B 2018/00875* (2013.01); *A61B 2018/00892* (2013.01); *A61B 2018/1455* (2013.01)
USPC .......................................................... 606/51

(58) Field of Classification Search
None
See application file for complete search history.

(56) References Cited

U.S. PATENT DOCUMENTS

| D249,549 | S | 9/1978 | Pike |
|---|---|---|---|
| D263,020 | S | 2/1982 | Rau, III |
| 4,655,216 | A | 4/1987 | Tischer |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| 5,122,137 | A | 6/1992 | Lennox |
| 5,190,541 | A | 3/1993 | Abele et al. |
| D343,453 | S | 1/1994 | Noda |
| D348,930 | S | 7/1994 | Olson |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Brian T Gedeon

(57) ABSTRACT

An end effector assembly adapted to couple to an electrosurgical instrument, the end effector assembly including a pair of opposing jaw members pivotably attached about a pivot member and moveable from a first spaced position to a second grasping position. Each jaw member includes a jaw housing and a seal plate formed on an inner surface of the jaw member including at least two seal plate segments extending along a substantial portion of the length of the jaw members. An insulating member is positioned between adjacent seal plate segments and configured to provide electrical isolation between adjacent seal plate segments. Each sealing plate segment is adapted to selectively connect to an electrosurgical energy source and form part of an electrosurgical energy delivery circuit.

19 Claims, 7 Drawing Sheets

(56) References Cited

U.S. PATENT DOCUMENTS

| | | | |
|---|---|---|---|
| D349,341 S | 8/1994 | Lichtman et al. |
| D354,564 S | 1/1995 | Medema |
| D358,887 S | 5/1995 | Feinberg |
| 5,443,463 A | 8/1995 | Stern et al. |
| 5,562,720 A | 10/1996 | Stern et al. |
| 5,582,611 A | 12/1996 | Tsuruta et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,976,492 B2 | 12/2005 | Ingle et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,621,910 B2 | 11/2009 | Sugi |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,909 B2 | 7/2010 | Chapman et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 2006/0052778 A1 | 3/2006 | Chapman et al. |
| 2009/0112200 A1 | 4/2009 | Eggers |
| 2010/0016857 A1* | 1/2010 | McKenna et al. ........... 606/51 |
| 2012/0059371 A1 | 3/2012 | Anderson et al. |
| 2012/0078250 A1 | 3/2012 | Orton et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |
| 2012/0209263 A1* | 8/2012 | Sharp et al. ............. 606/45 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 96/05776 | 2/1996 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2004/073490 | 9/2004 |
| WO | WO 2004/098383 | 11/2004 |
| WO | WO 2005/110264 | 11/2005 |
| WO | WO 2009/124097 | 10/2009 |

OTHER PUBLICATIONS

U.S. Appl. No. 09/177,9509, filed Oct. 23, 1998, Randel A. Frazier.
U.S. Appl. No. 09/387,8839, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.

(56) References Cited

OTHER PUBLICATIONS

U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis Mo, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report Ep 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.

(56) References Cited

OTHER PUBLICATIONS

Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

MULTI-CIRCUIT SEAL PLATES

BACKGROUND

1. Technical Field

The present disclosure relates to electrosurgical instruments used for open and endoscopic surgical procedures. More particularly, the present disclosure relates to an apparatus with multi-circuit seal plates, method of manufacturing multi-circuit seal plates and methods of sealing tissue with multi-circuit seal plates.

2. Description of Related Art

Electrosurgical forceps utilize mechanical clamping action along with electrical energy to effect hemostasis on the clamped tissue. The forceps (open, laparoscopic or endoscopic) include electrosurgical sealing plates that engage tissue and deliver electrosurgical energy to the engaged tissue. By controlling the intensity, frequency and duration of the electrosurgical energy applied through the sealing plates to tissue, the surgeon can coagulate, cauterize, and/or seal tissue.

During an electrosurgical procedure, seal plates deliver electrosurgical energy and/or heat to tissue. Ideally, the seal plates evenly distribute energy and uniformly heats tissue positioned between the seal plates. The seal plates and varying tissue properties and thicknesses can result in uneven distribution of energy, uneven heating and generation of hot zones within or between the sealing plates. As a result, the uneven distributed of energy may result in a longer duration sealing procedure and/or may result in a low-quality seal.

Additionally, a surgical procedure may often require several energy delivery sequences. The seal plates are heated during each electrosurgical energy delivery sequence and the time between each electrosurgical energy delivery may be insufficient to cool the seal plates. As such, thermal energy may accumulate during subsequent energy delivery sequences thereby resulting in a higher than desired temperature for the seal plates and a higher than desired temperature of tissue positioned between the seal plates.

SUMMARY

According to an aspect of the present disclosure, an end effector assembly adapted to couple to an electrosurgical instrument includes a pair of opposing jaw members pivotably attached about a pivot member and moveable from a first spaced position to a second grasping position. Each jaw member includes a jaw housing and a seal plate formed on an inner surface of the jaw member. The seal plate includes at least two seal plate segments extending along a substantial portion of the length of the jaw members. The jaw member also includes an insulating member positioned between adjacent seal plate segments and configured to provide electrical isolation between adjacent seal plate segments. Each sealing plate segment is adapted to selectively connect to an electrosurgical energy source and form part of an electrosurgical energy delivery circuit.

Each jaw member may also include a seal plate mount configured to operably couple the seal plate and the jaw housing and further configured to electrically couple each of the two or more seal plate segments to an electrosurgical energy source. The seal plate mount may include one or more switch circuit boards disposed on and operably coupled atop each seal plate.

Each seal plate may include a first seal plate segment, a second seal plate segment and a middle seal plate segment operably coupled between the first and second seal plate segments. A first insulating member is positioned between the first seal plate segment and the middle seal plate segment to provide electrical isolation therebetween. A second insulating member is positioned between the second seal plate segment and the middle seal plate segment to provide electrical isolation therebetween. The first, second and middle seal plate segments on each opposing jaw member form a planar sealing surface. Each of the first, second and middle seal plate segments is configured to selectively form part of an electrosurgical energy delivery circuit for sealing tissue positioned between the pair of opposing jaw members.

The middle seal plate segments may be configured to form part of an electrosurgical energy delivery circuit for cutting tissue positioned between the pair of opposing jaw members. A middle seal plate segment may include a geometry that is raised with respect to the planar sealing surface. The geometry may form a ridge or may include a radius of curvature.

According to a further aspect of the present disclosure, an electrosurgical instrument includes a housing, a handle assembly, a shaft having a proximal end and a distal end, the proximal end operably coupled to the housing and the distal end operably coupled to an end effector assembly. The end effector assembly includes a pair of opposing jaw members pivotably attached about a pivot member and moveable from a first, spaced, position to a second, grasping, position. Each jaw member includes a jaw housing, a seal plate formed on an inner surface of the jaw member including at least two seal plate segments extending along a substantial portion of the length of the jaw members and an insulating member positioned between adjacent seal plate segments. The insulating members are configured to provide electrical isolation between adjacent seal plate segments. Each sealing plate segment is adapted to selectively connect to an electrosurgical energy source and form part of an electrosurgical energy delivery circuit.

The electrosurgical instrument may further include a seal plate mount formed on each of the pair of opposing jaw members. The seal plate mount is configured to operably couple the seal plate and the jaw housing and electrically couple each of the two or more seal plate segments to an electrosurgical energy source. A switch, formed in the housing, may operably couple to the seal plate mount. The seal plate mount may further include a circuit board that includes at least two circuit board switches operably coupled to the switch. The switch and circuit board switches may selectively couple each of the seal plate segments to the electrosurgical energy source.

According to a further aspect of the present disclosure, an electrosurgical instrument includes a first and second shafts pivotably attached to one another about a common pivot. Each shaft includes a jaw member on a distal end thereof that includes a jaw housing, a seal plate and an insulating member. Each seal plate is formed on an inner surface of the respective jaw member and includes two or more seal plate segments extending along a substantial portion of the length of the jaw member. An insulating member is positioned between adjacent seal plate segments and configured to provide electrical isolation therebetween. Each seal plate segment is adapted to selectively connect to an electrosurgical energy source and form part of an electrosurgical energy delivery circuit.

BRIEF DESCRIPTION OF THE DRAWINGS

Various aspects of the subject instrument are described herein with reference to the drawings wherein.

DETAILED DESCRIPTION

Figure 1A:
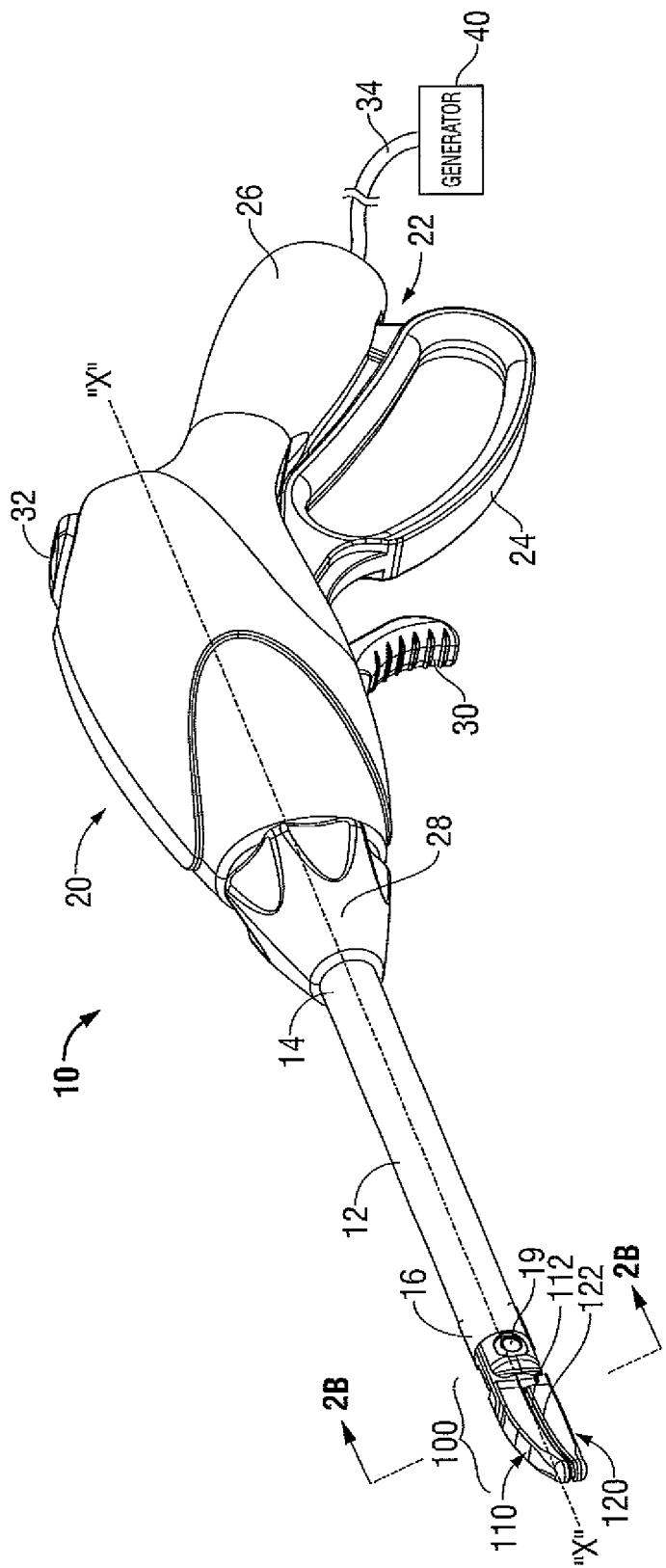
FIG. 1A is a perspective view of an endoscopic forceps having an end effector including multi-circuit seal plates in accordance with an aspect of the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

In accordance with the present disclosure, generally an end effector includes an upper seal plate and a lower seal plate described collectively as seal plates. The seal plates according to the present disclosure are manufactured to include a plurality of seal plate segments. The seal plate segments are configured to be selectively energized by a control circuit. Alternatively, two or more seal plate segments may be configured to be simultaneously energized by one or more electrical circuits. In this manner, tissue is selectively treated by one or more the individual seal plate segments or sequentially treated by one or more of the circuits that connect to the various seal plate segments. As such, the end effectors according to the present disclosure are configured and/or customized such that the tissue, or separate portions of the tissue, grasped between the jaw members, may be selectively treated.

Figure 1B:
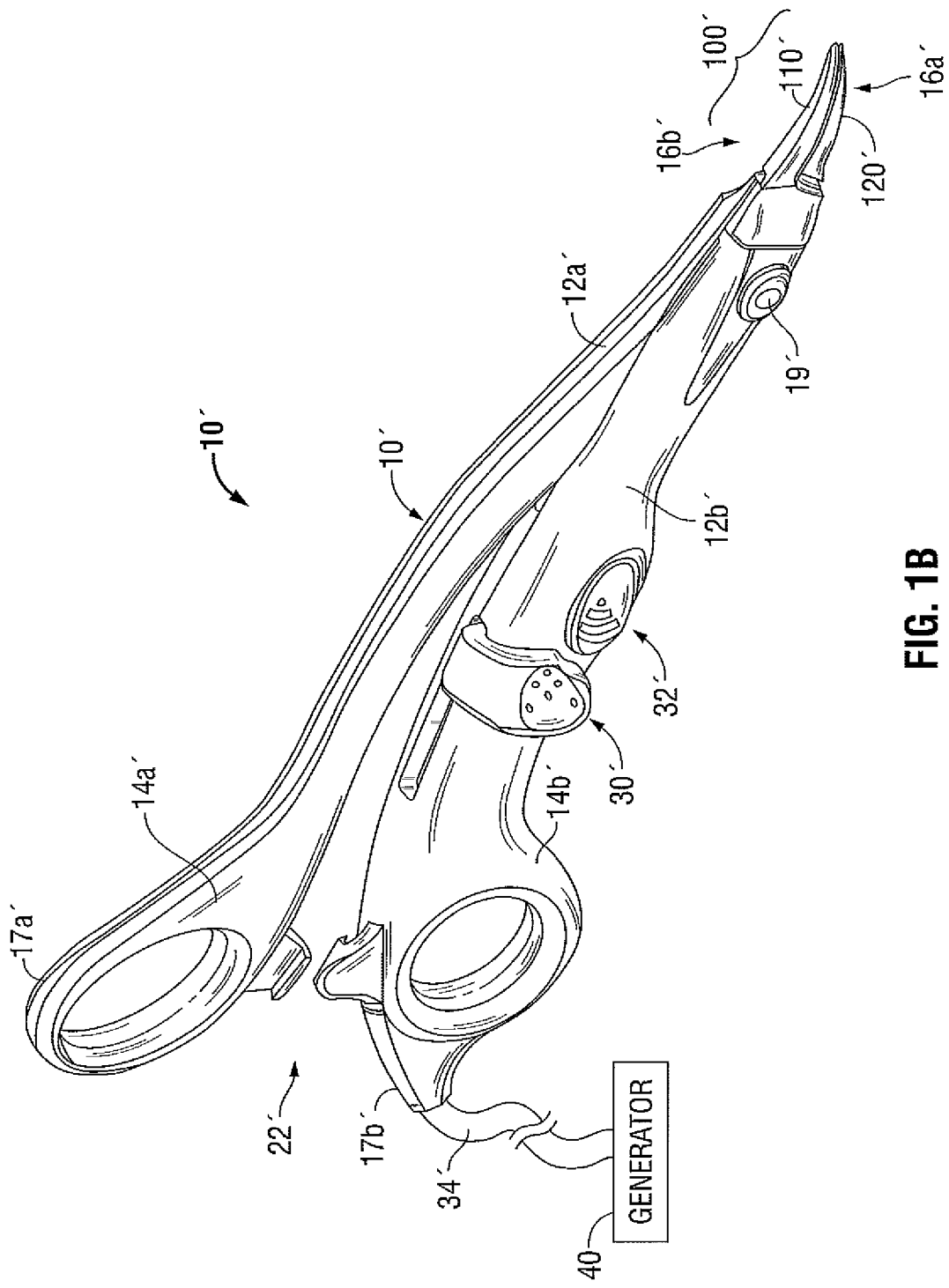
FIG. 1B is a perspective view of forceps for use in an open surgical procedure having an end effector including multi-circuit seal plates in accordance with an aspect of the present disclosure.

Referring now to the figures, FIG. 1A depicts an endoscopic forceps 10 for use in connection with endoscopic surgical procedures and FIG. 1B depicts an open forceps 10' for use in traditional open surgical procedures. For the purposes herein, either an endoscopic instrument, e.g., forceps 10, or an open surgery instrument, e.g., forceps 10', may utilize and end effector in accordance with the present disclosure. Obviously, different electrical, optical and mechanical connections and considerations apply to each particular type of instrument; however, the novel aspects with respect to the end effector assemblies described herein and their operating characteristics remain generally consistent with respect to both the endoscopic or open surgery designs.

Turning now to FIG. 1A, the endoscopic forceps 10 is coupled to an electrosurgical generator 40, or other suitable surgical energy source. Forceps 10 is adapted to seal tissue using radiofrequency (RF) energy or other suitable electrosurgical energy. Generator 40 is configured to provide electrosurgical energy at any suitable RF frequency.

Forceps 10 is coupled to generator 40 via a cable 34. Cable 34 is configured to transmit one or more RF energy signals and/or energy control signals between the generator 40 and the forceps 10. Forceps 10 may alternatively be configured as a self-contained instrument that includes the functionality of the generator 40 within the forceps 10 (e.g., an energy source, a signal generator, a control circuit, etc. . . . ). For example, forceps 10 may include a battery (not explicitly shown) that provides electrical energy, an RF generator (40) connected to the battery and configured to generate one or more RF energy signals and a microprocessor to perform measurement and control functions and to selectively delivery one or more RF energy signals to the end effector 100.

Forceps 10 include a housing 20, a handle assembly 22, a rotating assembly 28, a trigger assembly 30 and an end effector 100. Forceps 10 further include a shaft 12 having a distal end 14 configured to engage the end effector 100 and a proximal end 16 configured to engage the housing 20 and/or the rotating assembly 28. Cable 34 connects to wires (not explicitly shown) in the housing 20 that extend through the housing 20, shaft 12 and terminate in the end effector 100 thereby providing one or more electrical energy signals to the upper and lower sealing plates 112, 122.

Handle assembly 22 includes a fixed handle 26 and a moveable handle 24. Fixed handle 26 is integrally associated with housing 20 and moveable handle 24 is moveable relative to the fixed handle 26 to actuate the end effector 100 between an open condition and a closed condition and to grasp and treat tissue positioned therebetween. Rotating assembly 28 is rotatable in a clockwise and a counter-clockwise rotation to rotate end effector 100 about longitudinal axis "X-X". Housing 20 houses the internal working components of forceps 10.

Figure 2A:
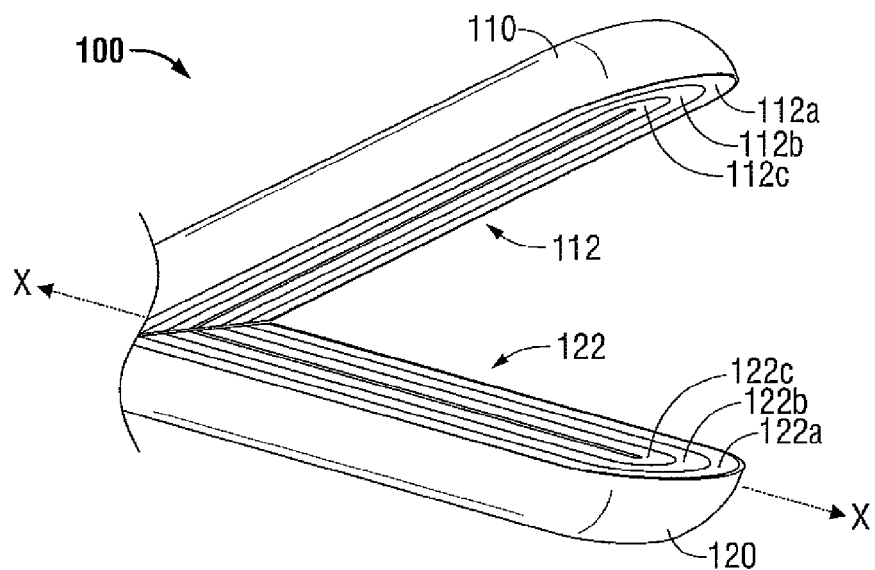
FIG. 2A is a perspective view of the end effector for use with the forceps of FIG. 1A and FIG. 1B in an open condition and including multi-circuit seal plates.
Figure 3A:
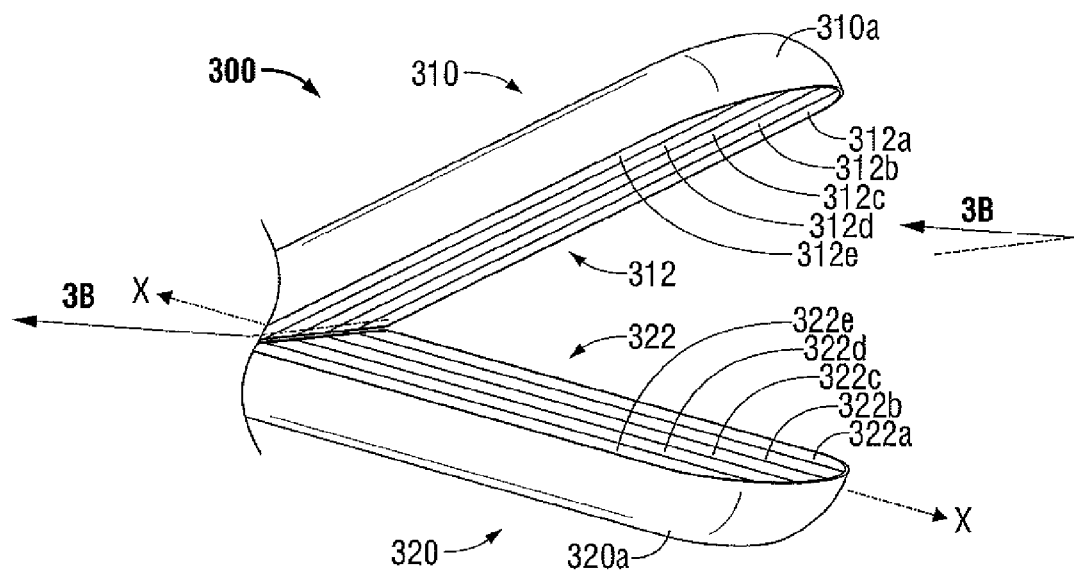
FIG. 3A is a perspective view of an end effector for use with the forceps of FIG. 1A and FIG. 1B in an open condition and including multi-circuit seal plates in accordance with a further aspect of the present disclosure.

End effector 100 includes upper and lower jaw members 110 and 120 are pivotable about a pivot 19 and are moveable between a first condition wherein jaw members 110 and 120 are closed and mutually cooperate to grasp, seal and/or sense tissue therebetween (See FIGS. 1A and 1B) and a second condition wherein the jaw members 110 and 120 are spaced relative to another (See FIGS. 2A and 3A).

Each jaw member 110, 120 include a tissue contacting surface 112, 122, respectively, disposed on an inner-facing surface thereof. Tissue contacting surfaces 112 and 122 cooperate to grasp tissue positioned therebetween and are configured to coagulate and/or seal tissue upon application of energy from generator 40. Tissue contacting surfaces 112 and 122 may be further configured to cut tissue and/or configured to position tissue for cutting after tissue coagulation and/or tissue sealing is complete. One or more of the tissue contacting surfaces 112, 122 may form part of the electrical circuit that communicates energy through the tissue held between the upper and lower jaw members 110 and 120, respectively.

Trigger assembly 30 is configured to actuate a knife (e.g., knife assembly 186, See FIG. 2B) disposed within forceps 10 to selectively cut/sever tissue grasped between jaw members 110 and 120 positioned in the first condition. Switch 32 is configured to selectively provide electrosurgical energy to end effector assembly 100.

Referring now to FIG. 1B, an open forceps 10' is depicted and includes end effector 100' attached to a handle assembly 22' that includes a pair of elongated shaft portions 12a' and 12b'. Each elongated shaft portion 12a', 12b' include a respective proximal end 14a', 14b' and a distal end 16a', 16b'. The end effector assembly 100' includes upper and lower members 110', 120' formed from, or attached to, each respective distal end 16b' and 16a' of shafts 12b' and 12a'. Shafts 12a' and 12b are attached via pivot 19' and are configured to pivot relative to one another thereby actuating the jaw members 110', 120' between the first condition and the second condition, as described hereinabove.

Shafts 12a' and 12b' include respective handles 17a' and 17b' disposed at the proximal ends 14a' and 14b' thereof. Handles 17a' and 17b' facilitate scissor-like movement of the shafts 12a' and 12b' relative to each other, which, in turn, actuate the jaw members 110' and 120' between a first condition and a second condition. In the first condition, the jaws 110' and 120' cooperate to grasp tissue therebetween and, in a second condition, the jaw members 110' and 120' are disposed in spaced relation relative to one another.

In some aspects, one or more of the shafts, e.g., shaft 12a', includes a switch assembly 32' configured to selectively provide electrical energy to the end effector assembly 100'. Forceps 10' is depicted having a cable 34' that connects the forceps 10' to generator 40 (as shown in FIG. 1). Switch assembly 32' is configured to selectively delivery the electrically energy from the generator 40 to the seal plates (not explicitly shown, see seal plates 112, 122 in FIGS. 2A and 2B). Switch assembly 32' may also be configured to select the electrosurgical energy delivery mode and/or the delivery sequencing as will be discussed hereinbelow.

Trigger assembly 30' is configured to actuate a knife assembly 186, as described with respect to FIG. 2B hereinbelow, disposed within forceps 10'. The proximal end of the knife assembly 186 (See FIG. 2B) connects to trigger assembly 30' within the shaft 12b' of the forceps 10'. Knife assembly 186 extends through shaft 12b' and forms a distal cutting edge 184 on the distal end thereof (See FIG. 2B). Knife assembly 186, when actuated by trigger assembly 30', extends the distal cutting edge 184 distally through a knife channel 115 (see FIGS. 2A and 2B) to sever tissue positioned between the jaw members 110' and 120'.

Figure 2B:
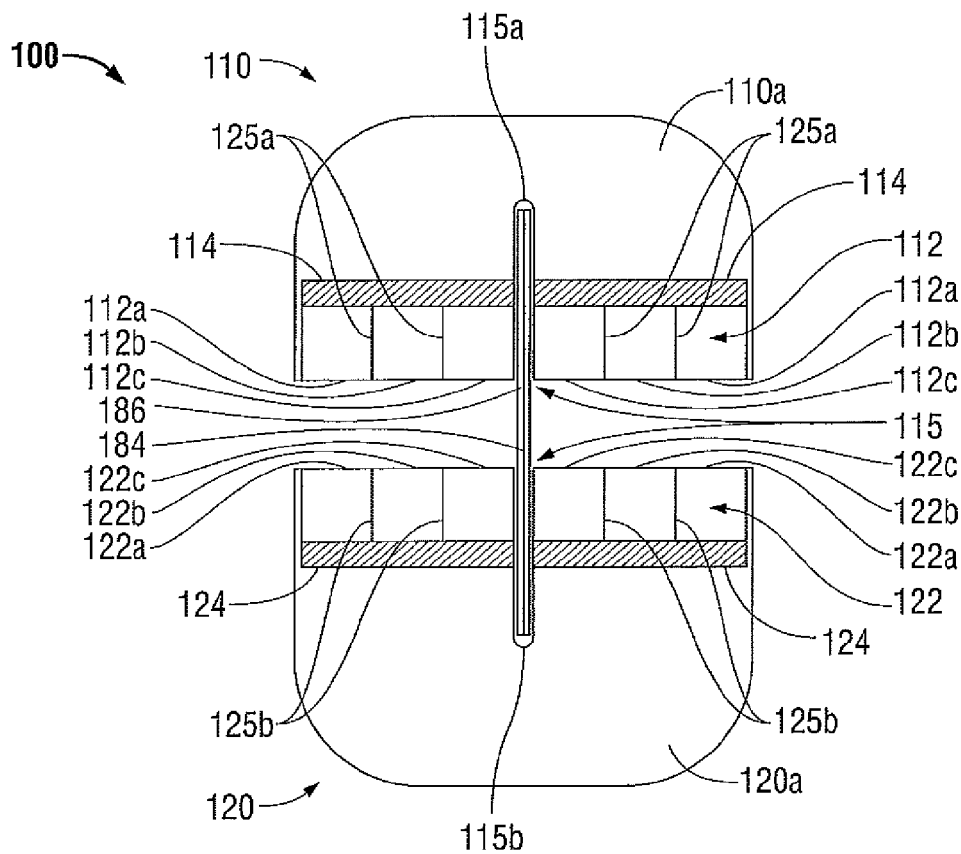
FIG. 2B is a front, cross-sectional view of the end effector of FIG. 2A in a closed condition.

With reference to FIGS. 2A and 2B, knife channel 115 is defined by a channel formed within one or both jaw members 110 and 120 to permit reciprocation of knife assembly 186 therethrough, e.g., via activation of the trigger assembly 30, 30' (See FIGS. 1A and 1B). The upper jaw member 110 and the lower jaw member 120, while in a first condition as illustrated in FIG. 2B, form knife channel 115 therebetween. Knife channel 115 includes an upper knife channel 115a, formed in the upper jaw member 110, mated with a lower knife channel 115b, formed in the lower jaw member 120.

Each seal plate 112, 122 may form a planar sealing surface that includes a plurality of seal plate segments 112a-112c and 122a-122c, respectively, electrically isolated from each other by insulating members 125a, 125b. Each seal plate segment 112a-112c and 122a-122c may form a substantially equal portion of the sealing surface (see FIG. 3A) or seal plate segments 112a-112c and 122a-122c may be unequally apportioned (see FIG. 2A).

Insulating members 125a and 125b may be formed from any suitable insulating material or dielectric material that provides electrical isolation between the middle seal plate segments 112b and 122b and the inner and outer seal plate segments 112a, 122a and 112c, 122c, respectively. Insulating members 125a and 125b may be formed from a polytetrafluoroethylene (PTFE), polypropylene, polychlorotrifluoroethylene (IPCTFE), polyethylene, polyethyleneterephthalate (PET), polyvinylchloride (PVC), a ceramic material or even air in a gap formed between adjacent seal segments.

The individual seal plate segments 112a-112c and 122a-122c may be pre-selected, or dynamically selected, as part of one or more electrical circuits that deliver electrosurgical energy to tissue positioned between the jaw members 110 and 120. For example, in one configuration the end effector 100 may include a first bipolar circuit that includes the outer seal plate segments 112a and 122a, a second bipolar circuit that includes the middle seal plate segments 112b and 122b and a third bipolar circuit that includes the inner seal plate segments 112c and 122c wherein the first, second and third bipolar circuits are independently enabled and/or controlled to deliver electrosurgical energy to tissue.

The seal plate segments on each jaw (e.g., lower seal plate segments 122a-122c on lower jaw 120) are arranged such that the seal plate segments are positioned radially outward from the lower knife channels 115b in a step-like manner. In this embodiment each seal plate segment forms a radius on the distal end thereof, thereby extending proximally along each side of the upper and lower jaw members 110 and 120. The seal plate segments 112a-112c on the upper seal plate 112 may have corresponding seal plate segments 122a-122c on the lower seal plate 122 positioned oppose and one another, as illustrated in FIG. 2B.

As shown by the cross-section of the end effector 100 in FIG. 2B, the inner surface of the seal plates 112 and 122 are each disposed on a seal plate mount 114 and 124, respectively. Each seal plate mount 114 and 124 may be formed as part of each seal plate 112 and 122, formed as part of the each jaw housing 110a and 120a or formed as separate components each configured to interconnect the seal plate 112 and 122 with the respective jaw housing 110a and 120a. Seal plate mount 114 and 124 may include a circuit, circuit board and/or connections that connects the seal plate segments (e.g., 112a-112c and 122a-122c) to the source of electrical energy (e.g., generator 40, See FIG. 1). Circuit, circuit board or connections may further include one or more switches (See multiplexer 60 in FIG. 6 and described hereinbelow) configured to selectably connect one or more seal plate segments 112a-112c and 122a-122c to the generator 40. The one or more switches may be controlled by the generator 40 or controlled/selected by the clinician (e.g., through the generator 40, the switch 32, switches in the seal plate segments or additional switching or selecting mechanisms on or in the forceps 10, 10').

Figure 6:
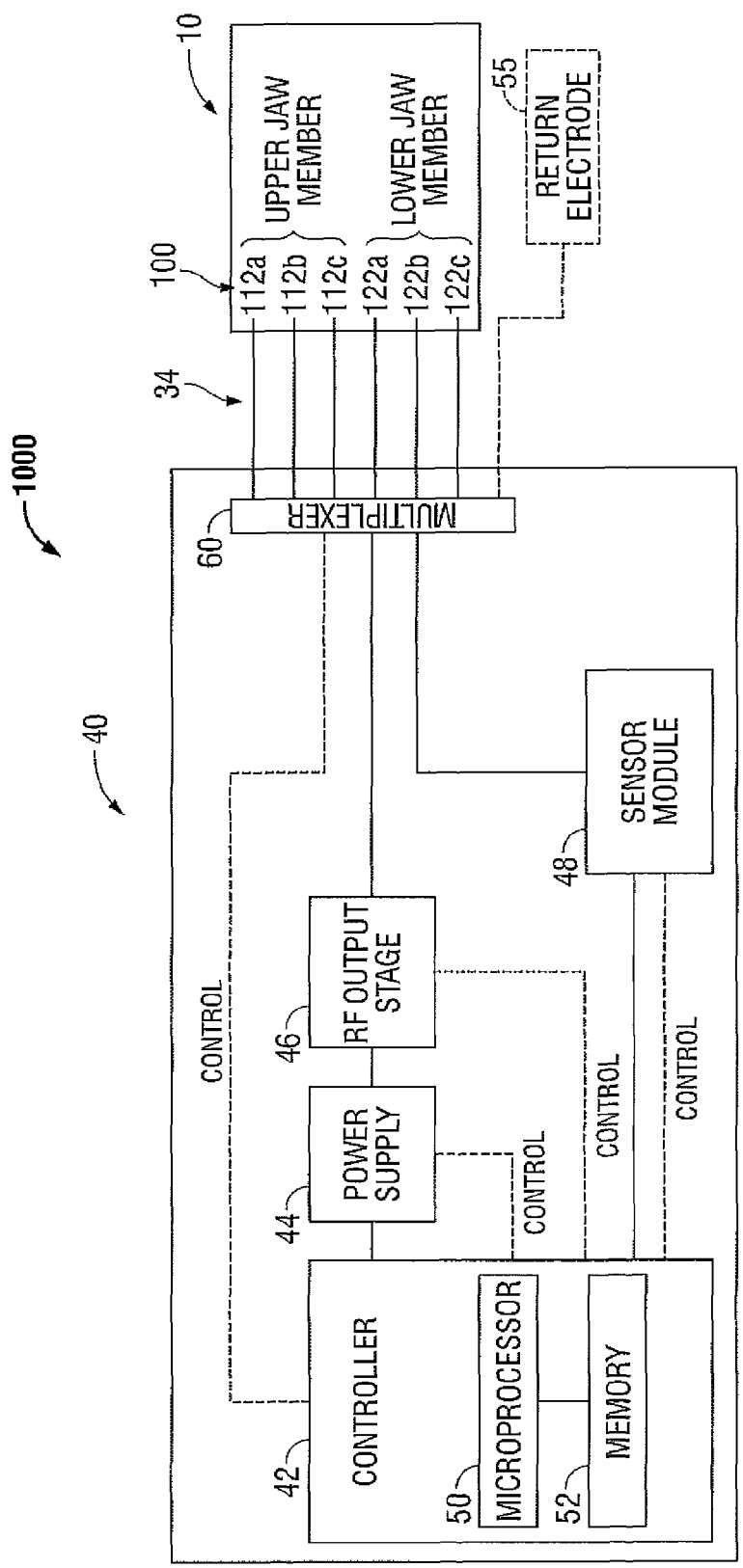
FIG. 6 is a schematic block diagram of an electrosurgical system for use with an end effector including multi-circuit seal plates according to a further aspect of the present disclosure.

In another embodiment, seal plates 112 and 122 mount directly to the respective jaw housing 110a and 120a and an electrical connection from the generator 40 connects directly to each seal plate segment 112a-112c and 122a-122c. A control circuit (See control circuit 42 in FIG. 6) may be configured to selectively form one or more electrosurgical energy delivery circuits with one or more of the seal plate segments 112a-112c and 122a-122c. The selected seal plate segments 112a-112c and 122a-122c can be configured to deliver electrosurgical energy to tissue in a monopolar or bipolar manner. As illustrated in FIG. 6, control circuit 42 may be housed in the generator 40 as stand-alone hardware or the functionality may be incorporated into the generator's 40 existing circuitry. Alternatively, as discussed hereinabove, the control and selection functionality described herein may be incorporated into the forceps 10.

The control circuit (e.g., controller 42; See FIG. 6) may be configured to dynamically select one or more of the seal plate segments 112a-112c and 122a-122c before and/or during the surgical procedure and may be configured to dynamically switch the selected seal plate segments 112a-112c and 122a-122c that form one or more of the electrosurgical energy delivery circuits. More specifically, the control circuit (e.g., controller 42) may be configured to provide electrosurgical energy to the first bipolar circuit during a first treatment cycle, configured to provide electrosurgical energy to the second bipolar circuit during a second treatment cycle and configured to provide electrosurgical energy to the third bipolar circuit during a third treatment cycle.

In another embodiment, the selected bipolar circuit does not include a corresponding seal plate segment on the upper and lower jaw members 110 and 120. For example, the bipolar circuit may include the outer seal segment 112a on the upper jaw member 110 and the middle and/or inner seal plate segment 122b and 122c on the lower jaw member 120 (See FIG. 2A). By forming a bipolar circuit in this manner (i.e., by not selecting corresponding seal plate segments on the upper and lower jaw members 110, 120) contact between the upper seal plate 112 and the lower seal plate 122 will not result in a short circuit between the selected portions of the upper and lower jaw members 110 and 120. As such, a stop member (not shown) that typically maintains a gap between the inner surface of the seal plates 112 and 122 and prevents contact between the seal plates 112 and 122 may not be required since contact between the seal plates 112 and 122 will not result in a short-circuit condition therebetween.

In another embodiment, the seal plate segments 112a-112c and 122a-122c selected to form a bipolar circuit are determined by a measured tissue parameter, wherein the measured tissue parameter is related to tissue positioned between the upper jaw member 110 and the lower jaw member 120. For example, the generator 40 (e.g., controller, 42 sensor module 48 and multiplexer 60) may be configured to measure the impedance of tissue positioned between two selected seal plate segments (e.g., upper seal plate segments 112a-112c and/or lower seal plate segments 122a-122c). Based on the measured value, the generator 40 may form one or more bipolar circuits between selected seal plate segments (e.g., upper seal plate segments 112a-112c and/or lower seal plate segments 122a-122c). The generator 40 may also generate an energy delivery sequence wherein the seal plate segments that form part of the one or more bipolar circuits are dynamically selected based on one or more measured tissue parameters. The generator 40 may also be configured to perform a subsequent measurement after energy delivery is initiated.

Generator 40 may perform a series of impedance measurements between the seal plate segments (e.g., upper seal plate segments 112a-112c and/or lower seal plate segments 122a-122c). The measurements may form a tissue impedance profile of the tissue positioned between the upper and lower jaw members 110 and 120. The tissue impedance profile may be utilized by the generator 40 to determine an energy delivery sequence specific to the tissue positioned between the upper and lower jaw members 110 and 120.

In another embodiment, seal plate segments 112a-112c and 122a-122c may be configured to energize from an outside-to-inside direction or from an inside-to-outside direction. For example, outer seal plate segments 112a and 122a may be initially energized for a first energization period, followed by a subsequent energization period wherein the middle seal plate segments 112b and 122b and/or the inner seal plate segments 112c and 122c are energized.

Figure 3B:
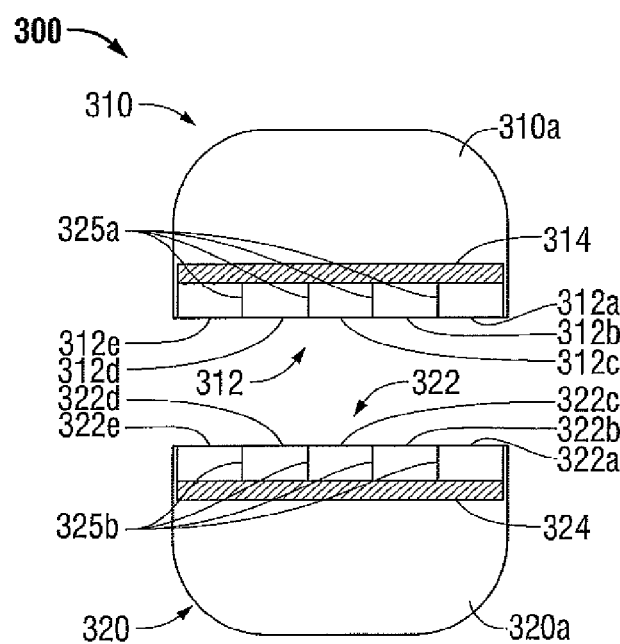
FIG. 3B is a front, cross-sectional view of the end effector of FIG. 3A in a closed condition.

FIGS. 3A and 3B illustrate a multi-circuit end effector assembly 300 according to another embodiment of the present disclosure. The end effector assembly 300 includes a pair of opposing jaw members 310 and 320 and opposing seal plates 312 and 322 housed in upper and lower jaw housings 310a and 320a, respectively. Upper and lower seal plates 312 and 322 each include a plurality of seal plate segments 312a-312e and 322a-322e, respectively, arranged on the inner surface of the seal plates 312 and 322, extending longitudinally along a substantial portion of the length of the jaw members 310 and 320 and parallel the longitudinal centerline X-X. Each seal plate 312, 322 forms a sealing surface (or substantially planar sealing surface) and includes a plurality of seal plate segments 312a-312e and 322a-322e, respectively, electrically isolated from each other by insulating members 325a and 325b. The seal plate segments 312a-312e and 322a-322e may form substantially equal or unequal portions of the sealing surface.

Seal plate segments 312a-312e and 322a-322e may be mounted on a respective seal plate mounts 314 and 324. Seal plate mount 314 and 324 may be formed as part of each respective seal plate 312 and 322, formed as part of each respective jaw housing 310a and 320a or configured to interconnect each seal plate 312 and 322 with the respective jaw housing 310a and 320a. Seal plate mount 314 and 324 may include a circuit or circuit board that provides an electrical connection to one or more of the seal plate segments (e.g., upper seal plate segments 312a-312e, lower seal plate segments 322a-322e). Seal plate mount 314 and 324 and/or circuit (or circuit board) formed therein provide an electrical connection between the source of electrical energy (e.g., generator 40, See FIG. 1) and the seal plates 312 and 322.

Seal plates 312 and 322 and/or seal plate mounts 314 and 324 may include one or more switches (not explicitly shown) configured to selectably connect one or more seal plate segments 312a-312e and 322a-322e to the source of electrical energy (e.g., generator 40 in FIG. 1; multiplexer 60 in FIG. 6). Switches may be automatically controlled by the generator 40 or selectable by the clinician through the generator 40 or through a switch (e.g., switch 32 or selector switch (not explicitly shown) formed on or in housing 20).

In one embodiment, the seal plate segments 312a-312e and 322a-322e are energized from an outside-to-inside manner or from an inside-to-outside manner. For example, corresponding upper and lower outer seal plate segments 312a and 322a, 312e and 322e may be initially energized for a first energization period, followed by a subsequent energization period wherein any one or more of the interior seal plate segments 312b-312d and 322b-322d, or combination thereof, are energized.

In a further embodiment, the upper and lower middle seal plate segments 312c and 322c may be configured to cut tissue positioned therebetween and the upper and lower outer seal plate segments 312a, 312b, 313d, 312e and 322a, 322b, 322d, 322e, respectively, are configured to seal tissue. The generator 40 may be configured to provide electrosurgical energy to seal tissue during a seal sequence and electrosurgical energy to cut tissue during a cut sequence. During the seal sequence, the generator 40 may provide an electrosurgical energy signal to select upper and lower seal plate segments 312a-312e and 322a-322e to coagulate and seal tissue. During a subsequent cut sequence, the generator 40 may provide an electrosurgical energy signal to the upper and lower middle seal plate segments 312c and 322c to cut tissue positioned therebetween. Providing a multi-circuit end effector 300 capable off electrosurgically sealing tissue during a first energy delivery period and capable of electrosurgical cutting tissue during a second energy delivery period eliminates the need for providing a means for mechanical cutting tissue (i.e., elimination of the trigger assembly 30' and knife assembly 186 of forceps 10', See FIGS. 1 and 2).

Figure 4A:
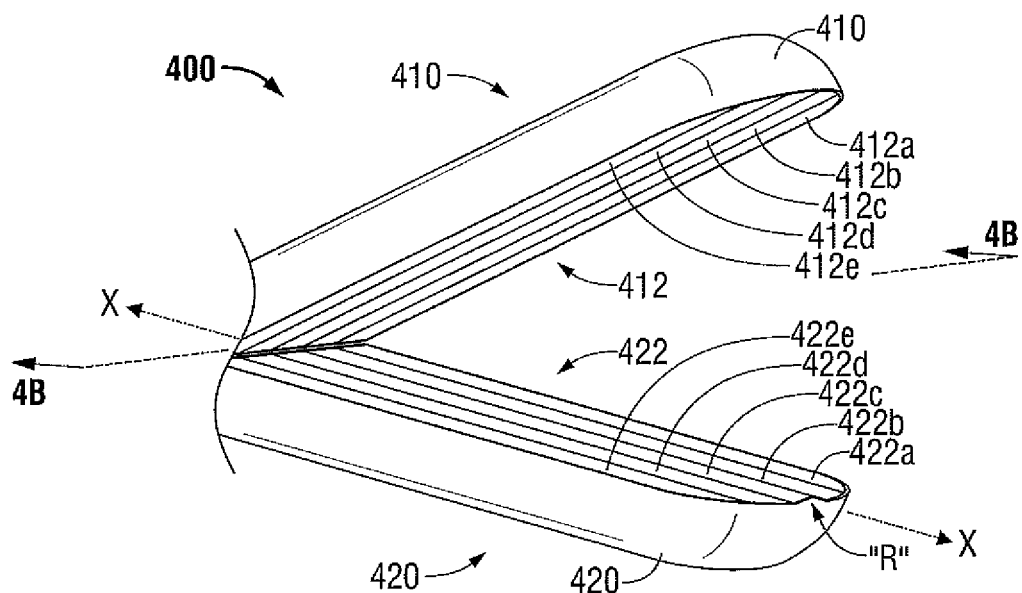
FIG. 4A is a perspective view of an end effector for use with the forceps of FIG. 1A and FIG. 1B in an open condition and including multi-circuit seal plates in accordance with a further aspect of the present disclosure.
Figure 4B:
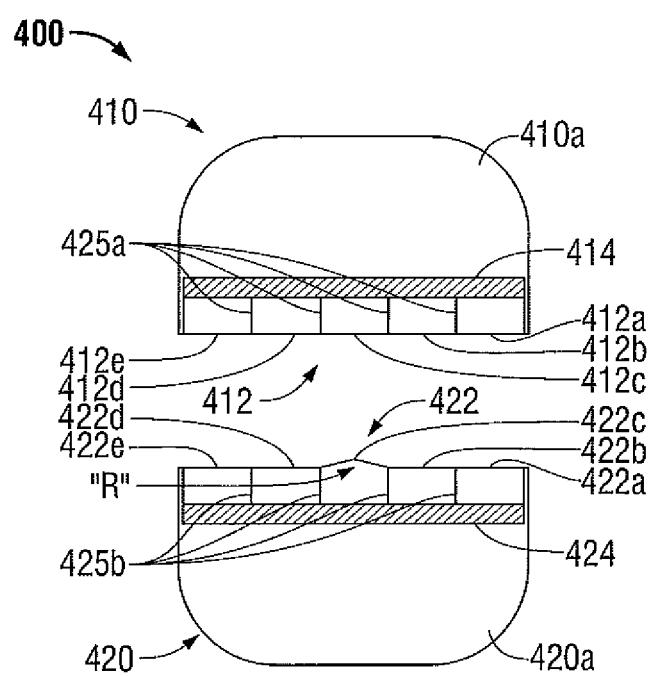
FIG. 4B is a front, cross-sectional view of the end effector of FIG. 4A in a closed condition.

FIGS. 4A and 4B illustrate a multi-circuit end effector assembly 400 according to a further embodiment of the present disclosure wherein the end effector assembly 400 includes a pair of opposing jaw members 410 and 420 and opposing seal plates 412 and 422 housed in upper and lower jaw housing 410a and 420a, respectively. Upper and lower seal plates 412 and 422 each include a plurality of seal plate segments 412a-412e and 422a-422e, respectively, arranged on the inner surface of the seal plates 412 and 422, extending the length of the jaw members 310 and 320 and parallel the longitudinal centerline X-X. Each seal plate 412 and 422 forms a sealing surface and includes a plurality of seal plate segments 412a-412e and 422a-422e, respectively, electrically isolated from each other by insulating members 425a and 425b. Each seal plate segment 412a-412e and 422a-422e may form a substantially equal or unequal portion of the sealing surface.

The upper or lower middle seal plate segments 412c and 422c may include a geometry configured to facilitate tissue cutting, in addition to tissue sealing, while the remaining outer seal plate segments 412a, 412b, 412d, 412e and 422a, 422b, 422d, 422e may include a geometry configured to facilitate tissue sealing. In this aspect, the lower middle seal plate segment 422c forms a ridge "R" wherein the ridge "R" is raised with respect to the sealing surface to facilitate tissue cutting during a second energization period as discussed above with respect to FIGS. 3A and 3B.

Upper and lower middle seal plate segments 412c and 422c may be included in a tissue sealing circuit in an initial tissue sealing stage and may form a tissue cutting circuit in a subsequent tissue cutting stage. For example, in an initial tissue sealing stage the upper middle seal plate segment 412c may form a sealing circuit with outer seal plate segment 412a and 422a and lower middle seal plate segment 412c may form a sealing circuit with the outer seal plate segments 412e and 422e. The sealing stage may include the selection of additional sealing circuits that may or may not include the upper and lower middle seal plate segments 412c and 422c. After the sealing stage is complete and the tissue positioned between the upper and lower jaws members 410 and 420 has been sufficiently sealed, a tissue cutting circuit that includes the upper and lower middle seal plate segments 412c and 422c is selected and upon activation thereof cuts the tissue positioned therebetween.

In a further embodiment, geometry, similar to the ridge "R" formed on the lower middle seal plate segment 422c of FIGS. 4A and 4B, forms a ridge on the upper and lower middle seal plate segments 412c and 422c wherein the geometries interface one another to facilitate cutting of the tissue positioned therebetween. For example, the upper and lower middle seal plate segments 412c and 422c may be arranged such that the geometry on each surface mates with the other along the inner-most surfaces or ridges. In a further embodiment, the upper and lower middle seal plate segments 412c and 422c include respective geometries that form a shearing interface therebetween thereby elimination or reducing the need for the tissue to be electrically energized to cut.

Figure 5A:
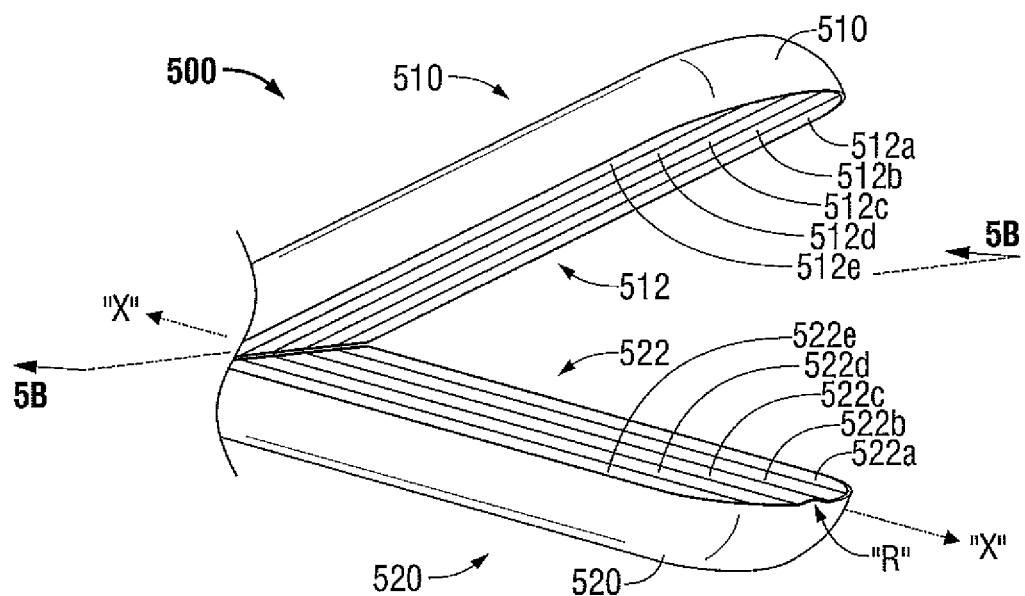
FIG. 5A is a perspective view of an end effector for use with the forceps of FIG. 1A and FIG. 1B in an open condition and including multi-circuit seal plates in accordance with a further aspect of the present disclosure.
Figure 5B:
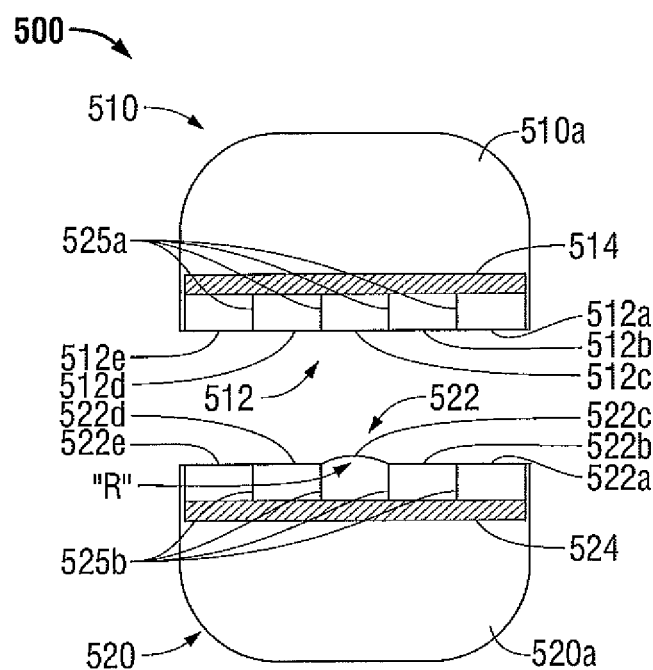
FIG. 5B is a front, cross-sectional view of the end effector of FIG. 5A in a closed condition.

FIGS. 5A and 5B illustrate a multi-circuit end effector assembly 500, similar to the multi-circuit end effector of FIGS. 4A-4B, wherein the geometry of the lower middle seal plate segment 522c includes a curved inner-most surface that is raised with respect to the sealing plate 522 to facilitate the cutting of tissue during a second energization period as discussed above with respect to FIGS. 3A and 3B. In a further embodiment the upper and lower middle seal plate segments 512c and 522c both include interfacing curved surfaces on the inner-most surfaces thereof.

As illustrated in FIGS. 4A-4B and 5A-5B, the geometry formed on the inner surface of the middle seal plate segments 422c, 522c provides a minimum separation distance between the upper and lower seal plates 412 and 422, 512 and 522, and is configured to seal tissue by delivering electrosurgical energy in an initial sealing stage and is configured to cut tissue by delivering electrosurgical energy in a subsequent tissue cutting stage.

In FIG. 6 a system schematic block diagram for driving an end effector according to the present disclosure is indicated as system 1000. System 1000 includes a generator 40, a forceps 10 with a multi-circuit end effector 100 connected by a cable 34. The generator 40 includes a controller 42, a power supply 44, an RF output stage 46, a sensor module 48 and a multiplexer 60. The power supply 44 provides DC power to the RF output stage 46 that converts the DC power into one or more RF energy signals. The one or more RF energy signals are individually provided to the multiplexer 60.

The controller 42 includes a microprocessor 50 having a memory 52 which may be volatile type memory (e.g., RAM) and/or non-volatile type memory (e.g., flash media, disk media, etc.). The microprocessor 50 includes a connection to the power supply 44 and/or RF output stage 46 that allows the microprocessor 50 to control the output of the generator 40 according to an open-loop and/or closed-loop control scheme. The power supply 44, RF output stage 46, multiplexer 60 and sensor module 48 are connected to, and controlled by, the controller 42 and configured to operate in concert to perform a selected surgical procedure.

For example, controller 42 may instruct the multiplexer 60 to connect an RF energy signal generated by the RF output stage 46 between any two or more segments of the end effector 100. For example, multiplexer 60 may be instructed by the controller 42 to form an electrosurgical energy delivery circuit between with outer seal segment 112a on the upper jaw member 110 and the inner seal portion 122c on the lower jaw member 120 (See FIG. 2A). Additionally, controller 42 may instruct the multiplexer 60 to connect the sensor module 48 between any two or more segments of the end effector 100 and controller 42 may instruct the sensor module 48 to perform a measurement between the selected segments of the end effector 100. For example, multiplexer 60 may be instructed by the controller 42 to form a measurement circuit between the middle seal plate segment 112b on the upper jaw member 110 and the middle seal plate segment 122b on the lower jaw member 120 (See FIG. 2A). Controller 42 may issue instructions to the various components in the generator 40 to performed energy delivery and measurements sequentially or simultaneously.

In a further embodiment, during operation the controller 42 may instruct the multiplexer 60 to direct an RF energy signal, generated by the RF output stage 46, to each of the first, second and third circuits during the respective first, second and third treatment cycles. The first, second and third treatment cycles may be executed consecutively, simultaneously or any portion of a treatment cycle may overlap with any other treatment cycle.

Controller 42, in executing a closed-loop control scheme, may instruct the multiplexer 60 to simultaneously connect two segments on the end effector 100 to the RF output stage 46 for delivery of electrosurgical energy and may further instruct the multiplexer to connect the sensor module 48 to two segments on the end effector 100 wherein the sensor module 48 provides feedback to the controller 42 for an energy delivery control loop (i.e., the sensor module 48 includes one or more sensing mechanisms/circuits for sensing various tissue parameters such as tissue impedance, tissue temperature, output current and/or voltage, etc.). The controller 42, using the energy delivery control loop, signals the power supply 44 and/or RF output stage 46 to adjust the electrosurgical energy signal.

The controller 42 also receives input signals from the input controls of the generator 40 and/or forceps 10, 10'. The controller 42 utilizes the input signals to generate instructions for the various components in the generator 40, to adjust the power output of the generator 40 and/or to perform other control functions. The controller 42 may include analog and/or logic circuitry for processing input signals and/or control signals sent to the generator 40, rather than, or in combination with, the microprocessor 50.

The microprocessor 50 is capable of executing software instructions for processing data received by the sensor module 48, and for outputting control signals to the generator 40, accordingly. The software instructions, which are executable by the controller 42, are stored in the memory 52 of the controller 42.

The sensor module 48 may also include a plurality of sensors (not explicitly shown) strategically located for sensing various properties or conditions, e.g., tissue impedance, voltage (e.g., voltage at the generator 40 and/or voltage at the tissue site) current (e.g., current at the generator 40 and/or current delivered at the tissue site, etc.) The sensors are provided with leads (or wireless) for transmitting information or signals to the controller 42. The sensor module 48 may include control circuitry that receives information and/or signals from multiple sensors and provides the information and/or signals, and/or the source of the information (e.g., the particular sensor providing the information), to the controller 42.

The sensor module 48 may include a real-time voltage sensing system and a real-time current sensing system for sensing real-time values related to applied voltage and current at the surgical site. Additionally, an RMS voltage sensing system and an RMS current sensing system may be included for sensing and deriving RMS values for applied voltage and current at the surgical site.

The generator 40 includes suitable input controls (e.g., buttons, activators, switches, touch screen, etc.) for controlling the generator 40, as well as one or more display screens for providing the surgeon with information (e.g., intensity settings, treatment complete indicators, etc.). The controls allow the surgeon to adjust power of the RF energy, waveform, and other parameters to achieve the desired waveform suitable for a particular task (e.g., surgical procedure such as tissue ablation, coagulation, cauterization, resection or any combination thereof). Further, the forceps 10, 10' may include one or more input controls, some of which may be redundant, with certain input controls included in the generator 40. Placing select input controls at the instrument 10, 10' allows for easier and faster modification of RF energy parameters during the surgical procedure without requiring interaction with the generator 40.

The generator 40 may be configured to perform monopolar and/or bipolar electrosurgical procedures. As illustrated in FIG. 6, multiplexer 60 may be configured to connect to a return electrode 55 thereby providing a return path for current during a monopolar energy delivery procedure wherein energy is delivered through one or more selected segments on the end effector 100 in a monopolar manner. The generator 40 may also include a plurality of inputs and/or outputs for interfacing with various electrosurgical instruments (e.g., footswitch, selector for selecting various electrosurgical modes such as cutting, blending, division, etc. and selector for selecting various procedures such as monopolar, bipolar, vessel sealing and ablation).

In any of the above-described embodiments, the seal plates or any seal plate segment thereof may be configured to seal sense and/or cut any type of tissue. In addition, any of the end effector assemblies described above may be configured to cut tissue with or without a knife.

With respect to sealing tissue, the gap between the seal plates (e.g., seal plates 112 and 122, see FIG. 2B) may be controlled by one or more stop members (not explicitly shown) on the inner surface thereof. Alternatively, the gap between the seal plates 412 and 422, 512 and 522 may also be controlled by the geometry of the Ridge "R" formed on the middle seal plate segment 422c and 522c. In addition, one or more devices, e.g., resilient members or the like, may be utilized to provide and/or control an appropriate pressure between the jaw members when the jaw members are in the clamping configuration. Further, one or more devices operably associated with the forceps 10 and 10' and/or the generator 40 may be configured to the control the amount of electrosurgical energy provided to the jaw members during a sealing stage, a cutting stage or during a stage that performs simultaneous sealing and cutting.

In another embodiment, seal plates according the present disclose may be configured to heat tissue. For example, seal plate assembly may be configured to include resistive heating capabilities instead of, or in addition to electrosurgical energy delivery capabilities.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications and combinations of the embodiments described herein are within the scope and spirit of the invention and the claims appended hereto.

What is claimed:

1. An end effector assembly comprising:
   a pair of opposing jaw members pivotably attached and moveable from a first spaced position to a second grasping position, each jaw member including:
   a jaw housing;
   a seal plate formed on an inner surface of the jaw member including at least two seal plate segments extending along a substantial portion of a length of the jaw members;
   an insulating member positioned between adjacent seal plate segments and configured to provide electrical isolation between the adjacent seal plate segments; and
   a seal plate mount configured to operably couple the seal plate and the jaw housing and further configured to electrically couple each of the at least two seal plate segments to an electrosurgical energy source,
   wherein the seal plate mount includes at least one switch circuit board disposed on and operably coupled atop the seal plate, and
   wherein each seal plate segment is adapted to selectively connect to the electrosurgical energy source and form part of an electrosurgical energy delivery circuit.

2. An end effector assembly according to claim 1, wherein each seal plate includes:
- a first seal plate segment,
- a second seal plate segment,
- a middle seal plate segment operably coupled between the first and second seal plate segment, within the seal plate,
- a first insulating member positioned between the first seal plate segment and the middle seal plate segment and providing electrical isolation therebetween, and
- a second insulating member positioned between the second seal plate segment and the middle seal plate segment and providing electrical isolation therebetween,
- wherein the first, second and middle seal plate segments on each opposing jaw member form a planar sealing surface.

3. An end effector assembly according to claim 2, wherein the first seal plate segments, the second seal plate segments and the middle seal plate segments are configured to selectively form part of an electrosurgical energy delivery circuit for sealing tissue positioned between the pair of opposing jaw members.

4. An end effector assembly according to claim 3, wherein each middle seal plate segment is configured to form part of an electrosurgical energy delivery circuit for cutting tissue positioned between the pair of opposing jaw members.

5. An end effector assembly according to claim 2, wherein the first seal plate segment, the second seal plate segment and the middle seal plate segment on each of the seal plates extends longitudinally along a substantial portion of the corresponding jaw member.

6. An electrosurgical instrument, comprising:
- a housing;
- a handle assembly;
- a shaft having a proximal and distal end, the proximal end operably coupled to the housing;
- an end effector assembly operably coupled to the distal end of the shaft, the end effector assembly comprising:
  - a pair of opposing jaw members pivotably attached and moveable from a first spaced position to a second grasping position, each jaw member including:
    - a jaw housing;
    - a seal plate formed on an inner surface of the jaw member including at least two seal plate segments extending along a substantial portion of a length of the jaw members;
    - an insulating member positioned between adjacent seal plate segments and configured to provide electrical isolation between adjacent seal plate segments;
  - a seal plate mount formed on each of the pair of opposing jaw members, the seal plate mount configured to operably couple the seal plate and the jaw housing and further configured to electrically couple each of the at least two seal plate segments to an electrosurgical energy source; and
- a switch formed in the housing and operably coupled to the seal plate mount, wherein the seal plate mount further includes a circuit board including at least two circuit board switches operably coupled to the switch, the switch and the at least two circuit board switches configured to selectively couple the at least two seal plate segments to the electrosurgical energy source, and
- wherein each seal plate segment is adapted to selectively connect to the electrosurgical energy source and form part of an electrosurgical energy delivery circuit.

7. An electrosurgical instrument according to claim 6, wherein each seal plate includes:
- a first seal plate segment;
- a second seal plate segment;
- a middle seal plate segment operably coupled between the first and second seal plate segments, within the seal plate;
- a first insulating member positioned between the first seal plate segment and the middle seal plate segment and providing electrical isolation therebetween; and
- a second insulating member positioned between the second seal plate segment and the middle seal plate segment and providing electrical isolation therebetween,
- wherein the first seal plate segment, the second seal plate segment and the middle seal plate segment on each opposing jaw member form a planar sealing surface.

8. An electrosurgical instrument according to claim 7, wherein the electrosurgical instrument further includes:
- a switch formed in the housing, the switch operably coupled to the seal plate;
- wherein the switch is configured to selectively couple at least two of the at least two seal plate segments to the electrosurgical energy source.

9. An electrosurgical instrument according to claim 7, wherein the first seal plate segment, the second seal plate segment and the middle seal plate segment are configured to selectively form part of an electrosurgical energy delivery circuit for sealing tissue positioned between the pair of opposing jaw members.

10. An electrosurgical instrument according to claim 9, wherein each middle seal plate segment is configured to form part of the electrosurgical energy delivery circuit for cutting tissue positioned between the pair of opposing jaw members.

11. An electrosurgical instrument according to claim 7, wherein each middle seal plate segment is configured to form part of an electrosurgical energy delivery circuit for cutting tissue positioned between the pair of opposing jaw members.

12. An end effector assembly comprising:
- a pair of opposing jaw members pivotably attached and moveable from a first spaced position to a second grasping position, each jaw member including:
  - a jaw housing;
  - a seal plate formed on an inner surface of the jaw member wherein each seal plate includes:
    - a first seal plate segment,
    - a second seal plate segment; and
    - a middle seal plate segment operably coupled between the first and second seal plate segments, within the seal plate;
  - a first insulating member positioned between the first seal plate segment and the middle seal plate segment and providing electrical isolation therebetween; and
  - a second insulating member positioned between the second seal plate segment and the middle seal plate segment and providing electrical isolation therebetween,
- wherein the first, second and middle seal plate segments on each opposing jaw member form a planar sealing surface, and
- wherein each seal plate segment is adapted to selectively connect to an electrosurgical energy source and form part of an electrosurgical energy delivery circuit.

13. An end effector assembly according to claim 12, wherein the first seal plate segments, the second seal plate segments and the middle seal plate segments are configured to selectively form part of the electrosurgical energy delivery circuit for sealing tissue positioned between the pair of opposing jaw members.

14. An end effector assembly according to claim 13, wherein each middle seal plate segment is configured to form part of the electrosurgical energy delivery circuit for cutting tissue positioned between the pair of opposing jaw members.

15. An end effector assembly according to claim 12, wherein the first seal plate segment, the second seal plate segment and the middle seal plate segment on each of the seal plates extends longitudinally along a substantial portion of the corresponding jaw member.

16. An electrosurgical instrument, comprising:
a housing;
a handle assembly;
a shaft having a proximal and distal end, the proximal end operably coupled to the housing;
an end effector assembly operably coupled to the distal end of the shaft, the end effector assembly comprising:
pair of opposing jaw members pivotably attached and moveable from a first spaced position to a second grasping position, each jaw member including:
a jaw housing;
a seal plate formed on an inner surface of the jaw member, wherein each seal plate includes:
a first seal plate segment;
a second seal plate segment; and
a middle seal plate segment operably coupled between the first and second seal plate segments, within the seal plate;
a first insulating member positioned between the first seal plate segment and the middle seal plate segment and providing electrical isolation therebetween; and
a second insulating member positioned between the second seal plate segment and the middle seal plate segment and providing electrical isolation therebetween,
wherein the first seal plate segment, the second seal plate segment and the middle seal plate segment on each opposing jaw member form a planar sealing surface, and
wherein each seal plate segment is adapted to selectively connect to an electrosurgical energy source and form part of an electrosurgical energy delivery circuit.

17. An electrosurgical instrument according to claim 16, wherein the electrosurgical instrument further includes:
a switch formed in the housing, the switch operably coupled to the seal plate,
wherein the switch is configured to selectively couple the at least two seal plate segments to the electrosurgical energy source.

18. An electrosurgical instrument according to claim 16, wherein the first seal plate segment, the second seal plate segment and the middle seal plate segment are configured to selectively form part of the electrosurgical energy delivery circuit for sealing tissue positioned between the pair of opposing jaw members.

19. An electrosurgical instrument according to claim 18, wherein each middle seal plate segment is configured to form part of the electrosurgical energy delivery circuit for cutting tissue positioned between the pair of opposing jaw members.

* * * * *